United States Patent
Maier

(10) Patent No.: US 8,569,010 B2
(45) Date of Patent: Oct. 29, 2013

(54) MASS SPECTROMETRIC DIAGNOSIS OF SEPTICEMIA

(75) Inventor: Thomas Maier, Leipzig (DE)

(73) Assignee: Bruker Daltonik GmbH, Bremen (DE)

( * ) Notice: Subject to any disclaimer, the term of this patent is extended or adjusted under 35 U.S.C. 154(b) by 95 days.

(21) Appl. No.: 13/322,363

(22) PCT Filed: Jul. 14, 2010

(86) PCT No.: PCT/EP2010/060098
§ 371 (c)(1),
(2), (4) Date: Jan. 6, 2012

(87) PCT Pub. No.: WO2011/006911
PCT Pub. Date: Jan. 20, 2011

(65) Prior Publication Data
US 2012/0115182 A1    May 10, 2012

(30) Foreign Application Priority Data

Jul. 16, 2009 (DE) .......................... 10 2009 033 368

(51) Int. Cl.
| | |
|---|---|
| C12Q 1/04 | (2006.01) |
| C12Q 1/24 | (2006.01) |
| C12Q 1/10 | (2006.01) |
| A01N 1/02 | (2006.01) |
| C12Q 1/00 | (2006.01) |
| C12Q 1/02 | (2006.01) |
| C12Q 1/14 | (2006.01) |

(52) U.S. Cl.
USPC .......... 435/34; 435/2; 435/4; 435/30; 435/36; 435/38

(58) Field of Classification Search
USPC ............................. 435/2, 4, 30, 34, 36, 38, 40
See application file for complete search history.

(56) References Cited

U.S. PATENT DOCUMENTS

| | | | |
|---|---|---|---|
| 4,753,749 A | 6/1988 | McIntosh | |
| 5,336,671 A | 8/1994 | Becher et al. | |
| 6,177,266 B1 * | 1/2001 | Krishnamurthy et al. | 435/173.1 |
| 2010/0255527 A1 | 10/2010 | Weller | |

FOREIGN PATENT DOCUMENTS

| | | |
|---|---|---|
| WO | 0221108 | 3/2002 |
| WO | 2010062352 | 6/2010 |
| WO | 2010100612 | 9/2010 |

OTHER PUBLICATIONS

Jha et al. 1999. Effect of Antifoaming Agents on the Micellar Stability and Foamability of Sodium Dodecyl Sulfate Solutions. Langmuir, vol. 15, pp. 3042-3044.*
Yeh et al. 2009.Hair Sheep Blood, Citrated or Defibrinated, Fulfills All Requirements of Blood Agar for Diagnostic Microbiology Laboratory Tests. PLOS ONE, vol. 4, No. 7, Published Jul. 3, 2009.*
Marklein et al. 2009. Matrix-Assisted Laser Desorption Ionization-Time of Flight Mass Spectrometry for Fast and Reliable Identification of Clinical Yeast Isolates. Journal of Clinical Microbiology, vol. 47, No. 9, pp. 2912-2917. Published on Line on Jul. 1, 2009.*
Carbonnelle et al. 2007. Rapid Identification of Staphylococci Isolated in Clinical Microbiology Laboratories by Matrix-Assisted Laser Desorption Ionization—Time of Flight Mass Spectrometry. Journal of Clinical Microbiology, 45(7), pp. 2156-2161.*
Japanese Office Action Dispatch date Aug. 15, 2013.

* cited by examiner

*Primary Examiner* — Jon P Weber
*Assistant Examiner* — Kailash C Srivastava
(74) *Attorney, Agent, or Firm* — O'Shea Getz P.C.

(57) ABSTRACT

The invention mainly relates to the mass spectrometric identification of pathogens in blood cultures from blood-stream infections (septicemia). The invention provides a method with which microbial pathogens can be separated in purified form from blood after a relatively brief cultivation in a blood culture flask, without any interfering human proteins or any residual fractions of blood particles such as erythrocytes and leukocytes, and can be directly identified by mass spectrometric measurement of their protein profiles. The method is based on the use of relatively strong tensides to destroy the blood particles by dissolving the weak cell membranes and most of the internal structures of the blood particles; in spite of the fact that tensides are regarded as strong ionization inhibitors in MALDI and other ionization processes required for mass spectrometric measurements. This method allows unknown pathogens to be obtained in their pure form by centrifuging or filtration and to be identified on the taxonomic level of species or subspecies. Problems with DNA from high levels of leukocytes can be resolved by special measures. After sufficient cultivation, the identification in a mass spectrometric laboratory takes only half an hour.

19 Claims, 3 Drawing Sheets

MASS SPECTROMETRIC DIAGNOSIS OF SEPTICEMIA

PRIORITY INFORMATION

This patent application claims priority from PCT patent application PCT/EP2010/060098 filed Jul. 14, 2010, which claims priority to German patent application 10 2009 033 368.1 filed Jul. 16, 2009, both of which are hereby incorporated by reference.

FIELD OF INVENTION

The invention relates to the mass spectrometric identification of pathogens in blood cultures from bloodstream infections (septicemia).

BACKGROUND OF THE INVENTION

Many species of microorganism (termed microbes below), particularly including bacteria and single-cell fungi (as yeast or mold), but also algae and protozoa, can be identified mass spectrometrically with a high degree of certainty by breeding a colony in the usual way on a nutrient medium, then transferring small quantities of microbes from the colony to a mass spectrometric sample support plate, and measuring a protein profile directly with a mass—spectrometer. The mass spectrum particularly represents the masses and abundances of the different soluble proteins which are present in sufficiently high concentration in the microbes. This protein profile of the microbes is used to determine their identity by a similarity analysis with reference spectra from a spectrum library.

Specialized mass spectrometers for this purpose and corresponding evaluation and similarity analysis programs are commercially available. At present, this identification procedure proves to be highly successful and rapidly conquers the microbiological laboratories all over the world.

"Identification" of the microbes means categorizing them into the taxonomic hierarchical classification scheme: Domain (eukaryotes and prokaryotes), kingdom, phylum, class, order, family, genus, species and subspecies. The identification of a microbe sample involves determining at least the genus, usually the species, and if possible the subspecies or even the strain as well, which is important, for example, if different subspecies or strains have different pathogenicity. In a more general sense, an identification can also mean a characterization in terms of other, more individual characteristics of the microbes, for example the resistance of a microorganism against antibiotics.

The nutrient medium for the cultivation of a colony is usually contained as an agar in a Petri dish, which normally results in the growth of pure strains in the form of separated microbe colonies in around six hours to some days, depending on the reproductive power of the microbes. If the colonies superimpose or strongly mix, pure colonies can be obtained in a second cultivation, again carried out in the usual way. In a most simple method, some microbes transferred from a selected colony to the mass spectrometric sample support with a small swab are then sprinkled with a strongly acidified solution of a conventional matrix substance (usually α-cyano-4-hydroxy cinnamic acid, HCCA, or 2,5-di-hydroxybenzoic acid, DHB) for an ionization by matrix-assisted laser desorption (MALDI). The acid (usually formic acid or trifluoroethanoic acid) attacks the cell walls, and the organic solvent (usually acetonitrile) of the matrix solution can penetrate into the microbial cells and cause their weakened cell walls to burst. The sample is then dried by evaporating the solvent, which causes the dissolved matrix material to crystallize. Soluble proteins and, to a much lesser extent, other substances of the cells are embedded into the matrix crystals.

The matrix substance crystals with embedded analyte molecules are then bombarded with focused flashes of UV laser light in a mass spectrometer, creating ions of the analyte molecules in the hot plasma of the vapor cloud; these ions can then be separated according to their mass and measured in the mass spectrometer. Specialized MALDI time-of-flight mass spectrometers (MALDI-TOF-MS) are normally used for this purpose. The mass spectrum is the profile of the mass values of these analyte ions. These are quite predominantly protein ions, the ions with most useful information having masses of between 3,000 daltons and 15,000 daltons approximately. The protein ions in this method are predominantly only singly charged (charge number $z=1$), which allows for simply referring to the mass m of the ions instead of always using the term "mass-to-charge ratio" m/z, as is actually necessary and conventional with other types of mass spectrometry.

The profile of the proteins is very characteristic of the microbe species in question because each microbe species produces its own set of genetically predetermined proteins each having its own characteristic molecular mass. The abundances of proteins with higher concentrations which can be detected by mass spectrometry, are also widely genetically controlled and depend only slightly on the nutrient conditions or maturity of the colony. The protein profiles are similarly characteristic of the types of microbes as fingerprints are characteristic of individual humans Nowadays, reliable and validated libraries with well documented reference mass spectra of microbes are being thoroughly extended by many laboratories in public and private research institutions and in microbiological institutes of universities. The reference libraries must fulfill strong requirements to be medically and legally admissible.

This method of identification has proven to be extraordinarily successful. The certainty of a correct identification is far greater than that of the microbiological identification methods used until now. It has been possible to prove that the certainty of the identification was way above 95 percent for hundreds of different types of microbe. In most cases of doubt, where there were some deviations from results of microbiological identification methods used until now, genetic sequencing has confirmed the correctness of the mass spectrometric identification.

If the library does not contain a reference mass spectrum for a species of microbe under investigation (which occasionally happens due to the millions of microbe species and the limited size of the current spectral libraries), library searches can usually produce valuable classifications into the higher taxonomic levels of the genus or family of the microbes, because related microbes frequently contain a number of identical types of protein. These cases are increasingly rare, however; pathogenic microbes have now practically all been recorded in the form of reference spectra and can therefore usually be accurately identified down to the level of microbe species.

The method briefly described above of using a small swab to spread some microbes from a colony onto a sample spot of a mass spectrometric sample support which is then sprinkled with a matrix solution, is the simplest and, as yet, fastest type of sample preparation. If a colony is just visible after cultivation, it takes only one to two hours in maximum until the identification is complete even if hundreds of samples have to be analyzed at the same time. Mass spectrometric sample supports with 48, 96 or 384 sample spots each are commercially available; acquisition of mass spectra from these numbers of samples takes around half an hour to two hours. If the identification is urgent, individual microbe samples can be identified in a few minutes (albeit after cultivation, which is always time-consuming)

Other methods of sample preparation have also been investigated, such as extracting the proteins after the microbes have been destroyed by sonication or mechanical treatment, or methods for extracting the proteins from microbes after the cell walls, which are sometimes hard, have been weakened by aggressive acids. These disintegration methods are used when the normal method of swabbing fails because the cell walls of the microbes are not destroyed by sprinkling with the matrix solution. If the swab methods produce mass spectra which are good enough for a comparison, all the disintegration methods provide spectra which are very similar to those of the swab methods, they often even show a lower interfering background in the mass spectra.

Today, mass spectra of the microbe proteins are usually acquired in the linear mode of MALDI time-of-flight mass spectrometers (MALDI-TOF) because these have a particularly high detection sensitivity, even though the mass resolution and the mass accuracy of the spectra from time-of-flight mass spectrometers in reflector mode are much better. In reflector mode, only around one twentieth of the ion signals appear, however, and the detection sensitivity is one or two orders of magnitude worse. The high sensitivity is based on the fact that not only the stable ions but also the much more abundant fragment ions and even the neutral particles from a so-called "metastable" decay which occurs during the flight of the ions, are detected in the linear mode of a time-of-flight mass spectrometer. Secondary electron multipliers (SEM) are used as ion detectors, measuring molecular ions, fragment ions and neutral particles because they all generate secondary electrons on impact. All fragment ions and neutral particles generated after acceleration in the ion source from one species of parent ion have the same speed as the parent ions and thus arrive at the ion detector at the same time. The arrival time is a measure of the mass of the ions which were originally undecomposed.

The increased detection sensitivity is so crucial for many applications that one accepts many of the disadvantages of operating the time-of-flight mass spectrometers in linear mode, such as a significantly lower mass resolution, for example. The energy of the desorbing and ionizing laser is increased for these applications, something which increases the ion yield but also increases their instability, although this is of no consequence here.

Acquiring mass spectra with time-of-flight mass spectrometers generally requires that a very high number of individual spectra are measured and digitized in rapid succession, the individual spectra usually being added together by adding measurement points with the same time-of-flight to form a sum spectrum. The ions for each individual spectrum are generated by one laser flash from a UV pulse laser for each spectrum. The sum spectra have to be generated in this way because of the low dynamic range of measurement and high noise on the signal in the individual spectrum. A minimum of approximately 50, in some cases even 1,000 and more individual spectra are acquired here; a sum spectrum generally consists of several hundred individual spectra which modern mass spectrometers acquire and add together in a few seconds.

For the identification of microbes, usually mass spectra from around 2,000 daltons to high mass ranges of 20,000 daltons are measured. However, mass signals in the lower mass range up to around 3,000 daltons do not have a high degree of reliability because they originate to a large part from coating peptides externally attached to the microbes, from fatty acids depending on kind and availability of nourishment, and a variety of other substances which are present only by chance. The best identification results are obtained if only the mass signals in the mass range between 3,000 and 15,000 daltons are evaluated. The low mass resolution, which occurs for the reasons given, means that the isotope groups whose mass signals each differ by one dalton can no longer be resolved in this mass range. The mass signals, therefore, reflect the shape of the envelopes of the isotope groups.

This method of identifying microbes requires a pure culture of identical microbes, a so-called "isolate", in order to obtain a mass spectrum which is not superimposed with signals of other types of microbes. It turned out, however, that mass spectra of mixtures of two microbe species can also be evaluated by special methods and that both microbe species can be identified. The identification certainty suffers only slightly. If more than two microbe species contribute to the mass spectrum, the identification probability and identification accuracy decrease very strongly.

The identification of microbes is particularly important for infectious microbes within the blood stream, called septicemia. The microbes usually are released into the blood continuously or in batches from unknown focuses of infections. It is important here that pathogen species are identified very early to commence a targeted medical treatment with correct antibiotics as soon as possible.

The mass spectrometric identification method competes with PCR analysis, where certain genetic sequences of the microbe's DNA, which are characterized by selectively operating pairs of primers, are replicated by polymerase chain reaction (PCR). These methods are fast and can lead to results within a few hours. These PCR analytical methods, however, need some prior knowledge of species, genera, families or classes of the microbes in order to select correct primer pairs. In general, only a "coarse" classification is performed according to the characteristics gram-positive or gram-negative, for example. The determination on the level of a microbe species is only possible in individual cases and requires a very targeted approach based on assumptions. The method is usually limited to individual, frequently occurring and particularly dangerous pathogens such as *Staphylococcus aureus*, for example. Positive identifications of individual microbe species remain valuable lucky strikes. In cases of negative identification, the knowledge of the exclusion of such dangerous microbes is certainly also valuable, but does not provide a basis for a therapy. The accurate determination of the microbe species must then be left to the conventional microbiological methods, which can quite easily take three to five days, however.

German Patent Application DE 10 2007 058 516 A1 (WPO 2009/065580 A1) discloses a method that directly separates pathogens from body fluids by centrifugation or filtration so that microbes can be transferred from the deposits (centrifugation or filtration pellets) onto the sample support plate. A still better method, also described in the document, is to disintegrate the microbes of the deposits after removal of the supernatant still within the centrifugation tube, for example by adding a few microliters of a strongly acidified matrix solution, with subsequent transfer of the solution with the released proteins onto the mass spectrometric sample support plate. With centrifugation, this disintegration is even possible when no visible pellet is produced. The limit of visibility for a centrifugation pellet is around $10^6$ microbes; the detection limit, in contrast, is currently about $10^4$ microbes, but may be still improved in the future. $10^4$ microbes usually contain more than 100 picograms of soluble proteins, the mass spectrometric detection limit is far below this, however. Since a cultivation stage is not required for infections in clear body fluids, identification in the mass spectrometric laboratory with this method of direct centrifuging of the body fluids can performed within a few minutes.

This method of direct centrifugation or filtration of the microbes is successful because, in the vast majority of cases (far more than 70 percent), acute microbial infections in body fluids are caused by only one single microbe species. At a low percentage of around 15 percent two microbe species are involved, in these cases usually both can be recognized in the mass spectra. This species purity of the pathogens of acute infections is in sharp contrast to other occurrences of microbes in or on the human body—the approximately $10^{14}$ bacteria of the intestinal flora in a human intestine comprise at least 400 species of bacteria which live in equilibrium with each other, for example. But the method of direct centrifugation is only successful if these microbes are present in very high concentrations of more than $10^4$ microbes per milliliter which is very rare for internal body fluids. Body fluids are generally sterile, i.e., they usually do not contain any microbes.

As described in the cited document, this method of sedimenting the microbes in a centrifuge or micro-filter can be applied directly and with a high degree of success to all clear body fluids such as lymph, synovial fluid or cerebrospinal fluid (liquor) and even to excreted body fluids such as urine or lachrymal fluid. For body fluids containing endogenous particles, such as whole blood, for example, intermediate steps must be introduced of first growing the microbes by cultivating the blood, because the concentration of microbes are usually only in the range of 0.5 to 10 microbes per milliliter, and second to completely and thoroughly destroy the blood particles such as erythrocytes or leukocytes to thoroughly get rid of all human proteins. In the documents cited, this destruction is exemplarily done by addition of distilled water. The very delicate cell membranes of the human particles are easily destroyed by the osmotic pressure of the water entering, in contrast to the much harder cell walls of bacteria. By repeated addition of distilled water and centrifugation a sufficiently clean pellet should be obtained which should no longer contain any residues of the human particles.

However, experiments carried out in the applicant's laboratory with this method of adding distilled water did not succeed in providing sufficiently clean centrifuge deposits, even when the washing and centrifuging processes were repeated a few times. Even if the deposits did not retain a slightly reddish color, superimpositions with human protein signals always interfered with the microbial protein signals from these deposits to such an extent that an identification becomes uncertain.

There is a need for a fast method for the clean separation of the pathogens of a septicemia in blood, without any traces of remaining human proteins, so that mass spectrometric identification down to the level of species or subspecies and, in addition, other investigations of the pathogens become possible.

SUMMARY OF THE INVENTION

The invention is based on the method for the direct deposition through sedimentation or pelleting of the microbes from body fluids by centrifugation or filtration known from German Patent Application DE 10 2007 058 516 A1 (WPO 2009/065580 A1), but uses a solution of a strong tenside, i.e., an amphiphile, surface-active substance rather than pure distilled water for the destruction of the blood particles. Sodium dodecyl sulfate (SDS), a strong anionic tenside which is also used in biotechnology as a denaturing agent for proteins, has proven to be ideal, in spite of the facts that (1) traces of tensides are known to be ionization inhibitors for proteins and other analyte substances in ionization processes like MALDI, and (2) that strong tensides like SDS are known to kill microbes, i.e., they act bactericidal by destroying their reproduction capability.

In one embodiment, the tenside is added directly and without any further pre-treatment to around one milliliter of blood from a blood culture, and mixed well for ten to thirty seconds in a shaker. Preferably the tenside is added as a solution, for example in the form of 10 µl to 200 µl of a 5 to 20% aqueous SDS solution Immediately after mixing, the mixture is centrifuged for two minutes at 10,000 g and the supernatant is discarded. If the pellet is visible at all, the deposit shows a surprisingly clear white in most cases. To remove any traces of the tenside, the pellet is washed with a milliliter of distilled water and centrifuged again. The supernatant is removed again. The deposit can now simply be taken up with a few microliters of formic acid and acetonitrile and one to two microliters of the solution can be transferred to the mass spectrometric sample support where matrix solution is added, and dried.

Since all these preparatory steps can be carried out very quickly, sample preparations on the sample support plate are available for mass spectrometric measurements after fifteen minutes at maximum. The introduction of the sample support plate into the evacuated ion source of the mass spectrometer and the measurement also take only a few minutes so that the mass spectrometric identification will be available in less than half an hour. Surprisingly, clean mass spectra of the protein profiles of the microbes without any interfering signals of human proteins are obtained, and the measurement turns out to be highly sensitive, in spite of the intermediate use of tensides.

This method of sedimenting the microbes from a blood sample for mass spectrometric identification can only be carried out if the blood has a high microbe level with more than $10^4$ microbes per milliliter; usually this is not the case with original blood from a patient. In normal septicemia, the level of living and active microbes, measured in "colony forming units" (CFU), is between 0.5 and 10 CFU/ml, only infected children show levels up to and above 100 CFU/ml. The microbes in the blood, therefore, have to be cultivated with suitable additives by incubating the blood in suitable blood culture flasks at optimum temperature. This cultivation is well-known and significantly faster than the cultivation of cultures in Petri dishes and, especially for severe infections, usually provides sufficient microbes for the identification within a few hours up to a few days. Only very slowly growing microbes, e.g., some mycobacteria, require cultivation times of many days to some weeks.

This method has the unique advantage of classifying the microbes without any prior knowledge down to the level of microbe species or even subspecies. No morphological (or microscopic) inspections, biochemical basic reactions or other types of pretest are necessary. Knowing the microbe species, the physician treating the patient can then immediately commence a targeted therapy because, for most microbes, information is available about the antibiotics to which they respond. The resistances of this microbe species against antibiotics, which can differ from region to region or from hospital to hospital, are usually also known. The early commencement of targeted treatment of a patient who is in an intensive care unit with a septicemia is not only extremely beneficial for the patient (up to live-saving), but also strongly cost-saving.

Although dissolving blood particles by strong tensides, in particular by SDS, is known in microbiology, the method is usually not applied. U.S. Pat. No. 4,753,749 discloses microbiocidal cleaning agents and teaches that detergents exhibit a certain amount of microbiocidal activity that is not sufficiently high to inhibit the growth of all pathogenic microorganisms. U.S. Pat. No. 5,336,671 discloses the use of tensides and defoamers in fungicidal compositions. Strong tensides such as SDS are considered to be bactericidal, and the reproduction capability of the microbes is important for microbiological identification methods. This does not apply to the mass spectrometric identification method, however.

The invention is based in particular on dissolving the different types of blood corpuscles quickly and completely without destroying the microbes. The delicate cell membrane of the blood particles includes predominantly of phospholipids, which form a membrane by non-covalent bonds. Strong tensides, in particular SDS, dissolve all non-covalent bonds of proteins and lipids and destroy the quaternary and tertiary structure of the molecules. The cell membranes therefore completely dissolve. The internal structures of the blood particles are also destroyed by the SDS and dissolved, including the membrane of the cell nucleus and the chromosomes of the leukocytes. All these dissolved components are removed with the supernatant fluid after the centrifugation or by the filtration. Some complications with DNA from leukocytes are discussed below.

The cell walls of bacteria, on the other hand, are very stable; they include mainly cross-linked polymerized mureins. This covalently bound mesh withstands the dissolving effect of the tensides. For the subsequent mass spectrometric identification it is not important whether the microbes die (for instance by unfolding the tertiary or quaternary structure of the internal proteins) or remain able to reproduce during this method, as long as the proteins in the interior are not lost or changed in their primary structure. For many microbes, however, this short-term separation and isolation method according to the invention still leaves sufficient microbes which can be reproduced as isolates in a further cultivation.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
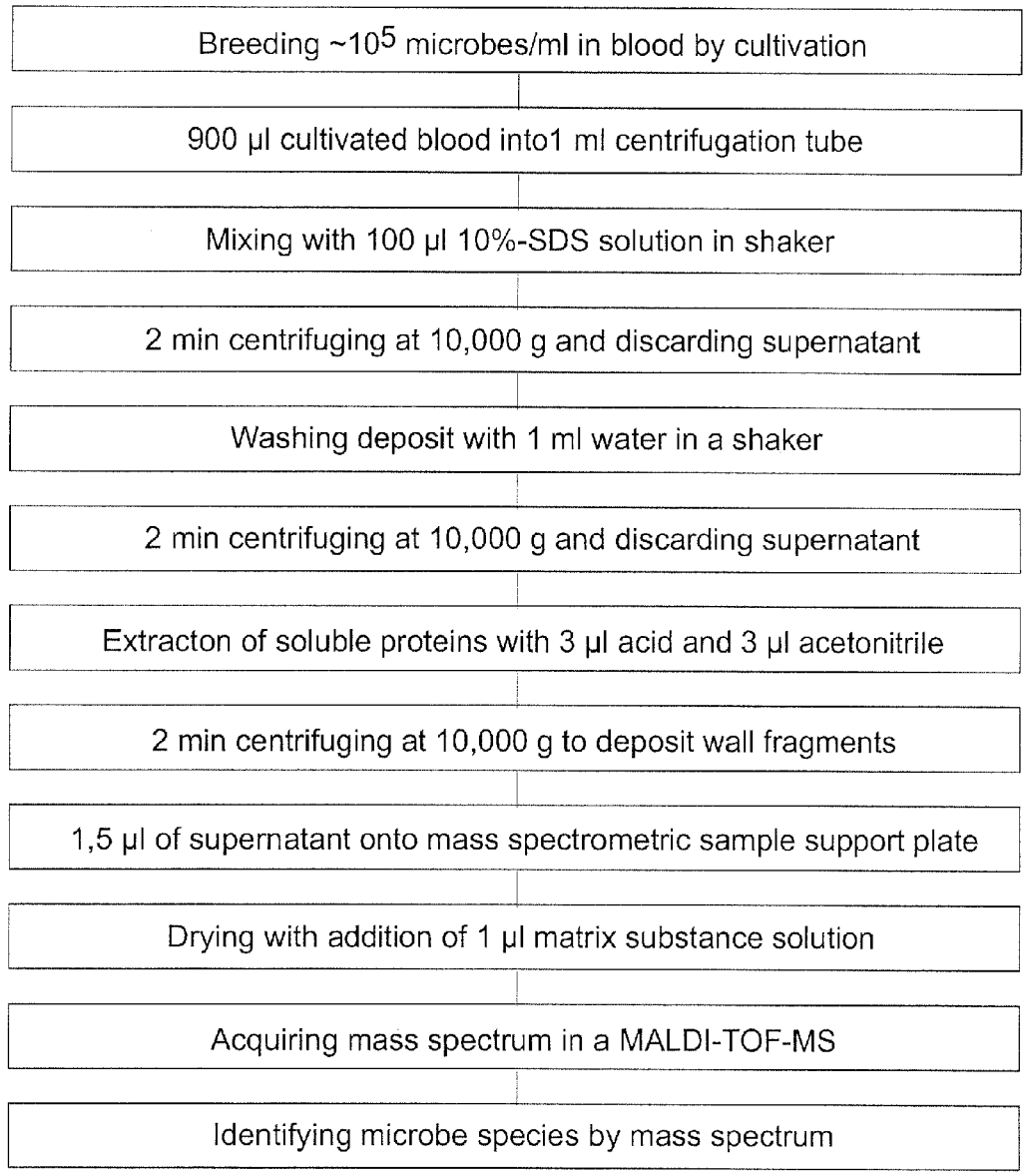
In FIG. 1, the simple basic procedure is outlined, known to be successful for blood of all patients with normal levels of leukocytes.
Figure 2:
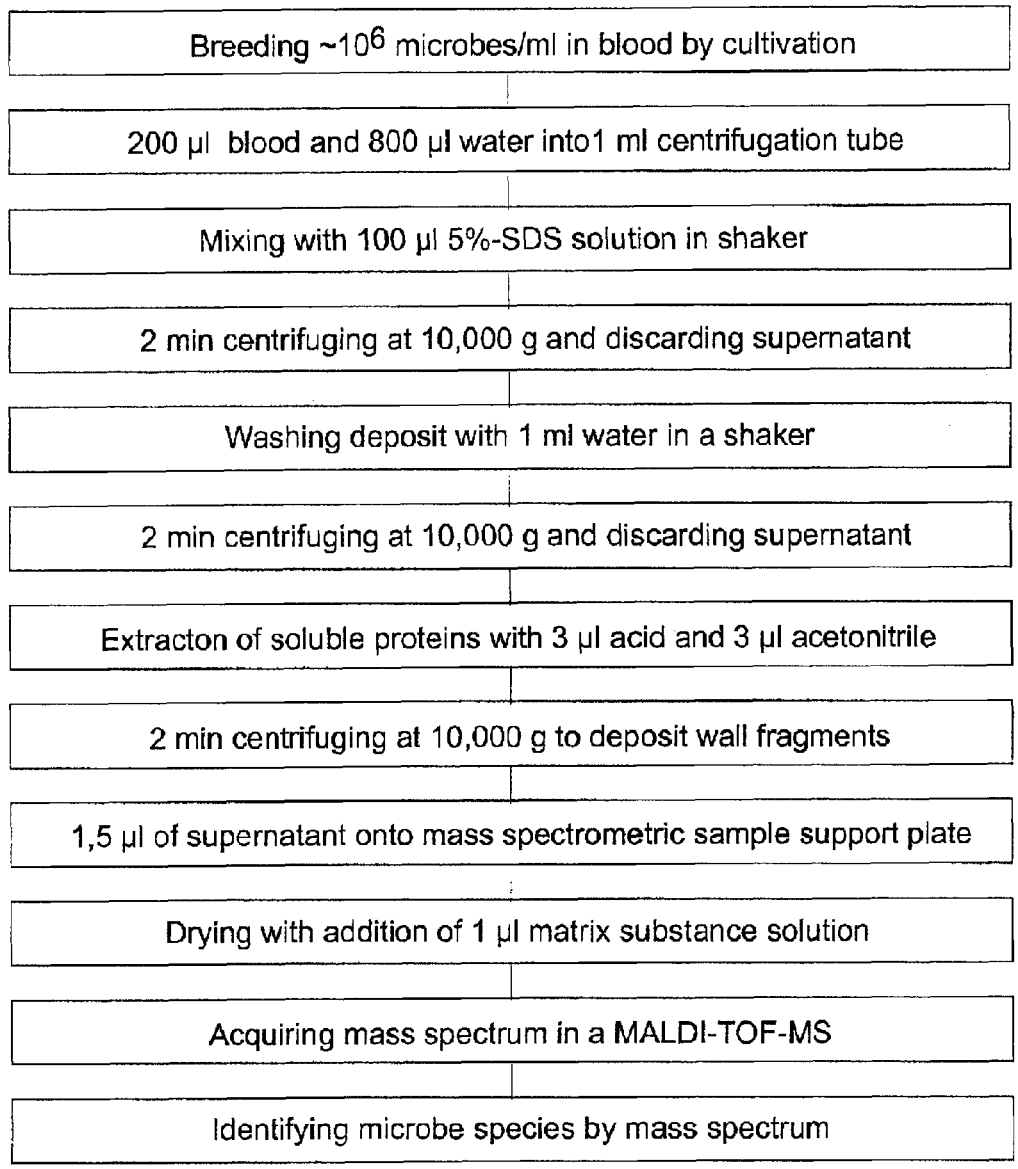
FIG. 2 shows a method to overcome problems with DNA agglutination for high-level leukocytes, but on costs of decreased sensitivity.
Figure 3:
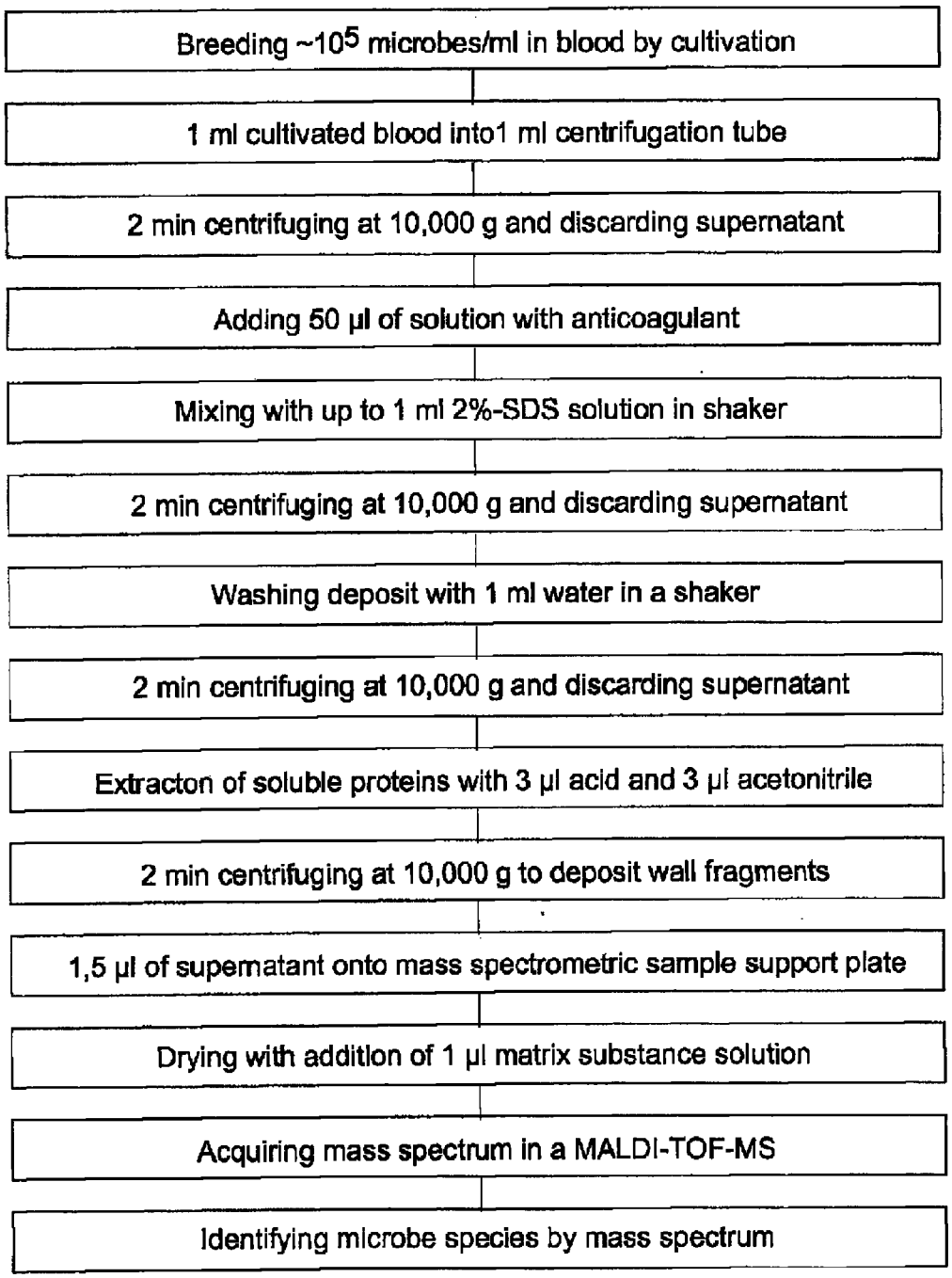
FIG. 3 presents a procedure with usual sensitivity which may be applied to all blood samples with high levels of leukocytes.

The preferred embodiments described below are based on blood samples which have a sufficiently high concentration of microbes with more than about $10^4$ microbes per milliliter. Only in extremely rare cases, this can be the delivered blood in the original state if the physician communicates an extremely acute infection; normally the method relates to the blood from a cultivation of several hours to a few days in appropriate blood cultivation flasks which are commercially available. The specialist knows, that the cultivation usually is performed for pairs of blood samples in pairs of blood cultivation flasks, one for aerobic microbes and one for anaerobic microbes. The flasks already contain anticoagulants and nutrients; after adding the blood they are incubated it in an incubator at 37° Celsius. In addition, the blood cultivation flasks already contain inhibitors or adsorption material for most antibiotics. Even if an immediate identification from the original blood is attempted (which may become possible more often in the future when the mass spectrometric detection sensitivity is sufficiently developed), it is expedient to cultivate the unused portion of the blood. This blood serves as a reserve in case the direct identification method with the original blood does not result in a sufficiently certain identification.

There are several types of special blood cultivation flasks commercially available having built-in indicators for a sufficient growth status of microorganisms. In most cases, these indicators are based on a measurement of the increasing concentration of carbon dioxide produced by the microorganisms. These blood cultivation flasks are easy to handle and indicate automatically sufficient reproduction of microbes by a signal. Investigations in the laboratories of the applicant, however, have shown that this signal comes rather late for mass spectrometric identifications. Successful identifications can already be obtained with cultivated blood two to four hours before the signal indicates sufficient reproduction of microbes. In cases of dangerous and critical septicemia, therefore, it may be opportune to try a mass spectrometric identification of the microbes in the cultivated blood every one or two hours, or other appropriate time intervals, not waiting for the signal.

An early method of obtaining microbes directly from blood (without in-blood culturing) for further cultivation on Petry dishes was developed by G. L. Dom around 1976, using lysis of the blood particles and soft centrifugation. The development of the lysis-centrifugation method resulted in the well-known "Isolator™" tubes, made commercially available first by DuPont (Wilmington, USA), then by Wampole Laboratories, Cranbury, N.J., USA, and nowadays also by Oxoid Limited, Basingstoke Hunt, England. Isolator™ is a trademark of Carter-Wallace, Inc., New York, N.Y. 10105 USA. During the past thirty years, many millions of Isolator™ tubes were used all over the world to separate microbes, particularly including mycobacteria freed from inside human macrophages, a kind of leukocytes. According to the "Wampole Isolator™ Manual", the Isolator™ tube contains (a) Saponin for host cell lysis, (b) Polypropylene glycol as foam retardant, (c) Sodium polyanethol sulfate (SPS) as anticoagulant, (d) EDTA as anticoagulant, (e) Fluorinert, a liquid plastic immiscible with water for the concentration of bacteria (as centrifugation cushion). There are different types of saponins, all of them are natural detergents (tensides) generated by different plants. The saponin inside the Isolator™ tube is a detoxified saponin, capable to dissolve the cell walls of the human blood particles without killing the microbes. The Isolator™ tubes are used for a soft centrifugation with only 3,000 g for a rather long time of 30 minutes, also with the intention not to damage the microbes. The aim of the method is the extraction of active microbes from blood for a recultivation of the microbes on suitable nutrients in Petry dishes.

In contrast to this method, the present invention aims for a fast recovery of purified microbes from cultivated blood for a mass spectrometric identification, with the absolute necessity to get rid of all traces of human proteins which otherwise would disturb the identification. The reproductive capability of the microbes which is important for microbiological identification methods, is not required for the mass spectrometric identification method, because here it is only the structural integrity of the cell walls and the chemical integrity of the internal protein molecules, and not the ability for reproduction which must be retained. For mass spectrometric identification it does not play any role if internal proteins are denaturized by unfolding their tertiary and quaternary structure. In the very fast method according to the invention described above, however, where the microbes are exposed to the SDS for only a few minutes at maximum, it turns out that many microbes retain their reproduction capability despite the antibiotic effect of SDS, and so the method of the separation and isolation of microbes from blood may also be used to provide further microbes in isolated form for other investigations like, for instance, resistance tests.

A simple, but already successful embodiment of the method of isolating and separating the microbes from cultivated blood is presented in FIG. 1. It starts with filling almost one milliliter of blood into each of several special centrifuge tubes, adding a tenside solution and mixing well. The tenside is preferably added as a solution, in the form of 20 to 200 microliters (preferably 100 microliters) of a 5 to 20 percent SDS solution (preferably 10 percent), for example. Filling several centrifuge tubes allows the centrifuge to be balanced and also makes it possible to immediately obtain confirmation samples for a reliable identification. After mixing for 10 to 30 seconds in a shaker, the blood sample is centrifuged in the centrifuge tubes for two minutes at 10,000 g. The deep-red supernatant liquid is removed, e.g., with a conventional pipette with removable tips. The deposit of microbes is now taken up and washed with distilled water; after further centrifugation a deposit of isolated microbes remains which, if visible at all, is purely white. Only in critical cases the washing procedure has to be repeated to get rid of all traces of human proteins; each washing process is prolonging the total procedure by about two to three minutes only.

Handling the SDS solution requires some caution because the solution easily foams up, and the stiff foam lasts for hours or even days, making it hard to use the liquid. In a preferred mode, a foam inhibitor (defoamer) may be added to the SDS solution. There are several types of defoamers on the market. The principle of the application of a defoamer is already known from Isolator™ tubes.

After the last removal of the supernatant, the soluble proteins of the microbes have to be extracted. This can be done by a destruction of the cell walls by physico-chemical means, and dissolving the proteins. Usually the extraction is simply performed by addition of around a few microliters of a 70 percent formic acid, which aggressively attacks the peptidoglycans (mureins) of the cell walls of the microbes and destroys the cell structure. The same quantity of acetonitrile is then added in order to dissolve as many proteins as possible. Only in rare cases, other techniques such as for example sonication or mechanical destruction are needed. The solution of the soluble proteins is centrifuged in order to precipitate the solid components such as cell wall fragments, for example, and about one microliter of the supernatant each is pipetted onto sample spots of a MALDI sample support plate. After drying, around one microliter of a solution of matrix substance, preferably HCCA or DHB dissolved in water and acetonitrile with a small amount of trifluoroethanoic acid, is added to each of the sample preparations. All these procedures are be carried out simultaneously for several centrifuge tubes which have been filled with blood samples. After drying, the sample preparations on the sample support plate are ready for the acquisition of mass spectra. If there are more blood samples to be analyzed, these can be worked on simultaneously, depositing the sample preparations on other sample spots of the same MALDI sample support plate.

There are different types of MALDI sample support plates commercially available, with 48, 96, and 384 sample spots. There are, for instance, sample support plates which contain hydrophilic anchor places about two millimeters in diameter in a hydrophobic environment. The transferred solution then forms a hemispheric droplet two millimeters in diameter on the anchor place. Other commercial sample support plates contain pre-fabricated matrix substance layers (HCCA) on the sample spots. Single-use sample support plates carry visible laser-etched rings with two millimeters in diameter which stop the spreading of the droplets. All these sample support plates can be used appropriately for the mass spectrometric measurement part of the methods according to the invention.

The simple preparation method for the measurement samples can be modified in a wide variety of ways. One option is to use the sample support plates which already carry a thin layer of the matrix substance, HCCA, for example. The supernatant of formic acid and acetonitrile is then pipetted directly onto this thin layer. The thin layer has the property of immediately adsorbing all proteins on the surface of the matrix crystals so that after around one minute the remaining liquid can be removed, e.g. by pipetting or simply with a blotting paper. This also removes impurities like salts or residual tensides. The subsequent optional addition of a droplet of acetonitrile can embed the proteins into the small crystals of the thin layer, thereby increasing sensitivity.

Instead of sedimenting the microbes by centrifugation, they can also be deposited and washed by micro-filtration. Since the addition of tensides causes the cell membranes of the blood particles and their internal structure to practically completely dissolve, a pure isolate of the microbes is also obtained by micro-filtration.

These processes for separating the microbes from blood and for preparing the measurement samples take only about 10 to 15 minutes in total. The sample support plate with the sample preparations is now introduced in the usual way via a vacuum lock into the ion source of a commercially available mass spectrometer. The mass spectrometer is operational in around five minutes. In a mass spectrometer whose UV pulse laser operates at 200 hertz it takes only a few seconds to acquire a sufficient number of individual spectra from a measurement sample in order to obtain a very usable sum spectrum. The acquisition of the mass spectra can therefore be completed after one minute. (Nowadays, MALDI-TOF mass spectrometers are commercially available with 2 kilohertz lasers).

Also commercially available are computer programs for the subsequent identification of the microbes by their mass spectra, e.g. the "Biotyper" (Bruker Daltonik, Bremen, Germany). The time required for the identification of the microbes from good mass spectra depends on the performance of the computer, the size of the library with reference spectra, and the algorithm for the similarity analysis. With commercially available computers in mass spectrometers the identification of the mass spectra from the samples including the confirmation samples takes only seconds up to a few minutes in maximum; the identification of the microbes is therefore available in digital or printed form half an hour after the end of a successful cultivation of the microbes in blood.

All these simple methods for obtaining pure deposits of microbes and subsequent identification by mass spectrometry work quite successful with blood from normal patients, being delivered the first time into a hospital. The identification success rate of this most simple embodiment of the invention amounts to more than 95 percent.

There are, however, very specialized hospitals of last resort, where patients with chronic and widely unknown diseases finally undergo thorough investigations and special treatment. In these kinds of hospital with patients of rare and difficult diseases, up to 40 percent of the blood samples, after being treated with SDS solution, form large mucous cots swimming invisibly in the deep red liquid. These mucous plugs entrain an unknown percentage of the microbes. A skilled person can pipette some fluid from around the plugs for further treatment, but this method is difficult and lowers the detection limit by unknown factors. An investigation suggests that these mucous cots mainly include DNA from highly increased numbers of leukocytes, possibly intermixed with coagulated proteins from the blood. The patients usually show highly increased levels of leukocytes in their blood.

There are several solutions to this problem. As a first and very simple solution, the blood may be diluted by a factor between two and ten, preferably of about five, with distilled water, before the SDS solution is added. Diluting by a factor of five increases the success rate to more than 90 percent, but also decreases the sensitivity of the method by a factor of five if the same 1 ml centrifugation tubes are used. In critical cases, the corresponding prolongation of the cultivation time which is necessary to produce more microbes, may be unbearable.

As a second solution for the clotting problem, a method of centrifuging the blood sample before adding the SDS solution can be used. The success rate is improved, probably by removal of all coagulating proteins of the blood before addition of the SDS solution. In this embodiment, which may be introduced as a standard procedure at special hospitals, the blood initially filled into the centrifuge tubes will be centrifuged first without the addition of tenside solution. The supernatant clear blood plasma with its hundreds of proteins, added nutrients and anticoagulants is then removed and only the deep-red deposit is taken up with a tenside solution, a 1 percent SDS solution, for example, filling the tube up to one milliliter in total. The deep-red deposit, which contains not only the microbes but normally also the 5 million erythrocytes, 7 thousand leukocytes and 200 thousand thrombocytes from the one milliliter of blood, is mixed with the added tenside solution in a shaker, thereby destroying the cell membranes of the blood corpuscles and releasing the soluble proteins. The deep-red solution is now centrifuged again, the supernatant remaining deep red this time and the deposit, if visible, appearing purely white. The process of removing the supernatant, filling up with tenside solution and centrifuging may now be repeated to remove even the last residues of blood particles. The process may then be repeated with pure distilled water to remove the tenside, because it would interfere with the ionization by matrix-assisted laser desorption (MALDI). After a last removal of the supernatant the deposit, whether visible or not, is disintegrated as described above and the soluble proteins are transferred onto the sample support plate.

As a third solution for the problem of blood clotting, the SDS solution may be prepared with special anticoagulants to inhibit the formation of the mucous plugs. This problem solution may be combined with the second problem solution.

As a fourth solution, the mucous plugs may be dissolved by addition of one or more nucleases.

If the deposit is visible after the final washing step, a different embodiment of the invention can be applied, including the transfer of a small quantity of the microbes thus isolated with a swab onto the sample support plate where they can be prepared as usual. The mass spectra of this conventional swab technique are to a large extent similar to the mass spectra of the disintegration technique using acid in the centrifuge tube. If differences are evident here, mass spectra of both types of sample preparation can be entered as reference spectra into the library.

The invention provides a method for the reliable identification of microbial pathogens in blood which is significantly simpler and faster than previous microbiological methods, which are practically always carried out via a cultivation of the microbes on gels in Petri dishes. The invention obtains the purified microbes directly from the blood after a cultivation procedure, where they are present in sufficient species purity, which is not the case for microbes occurring in or on other locations of the human body. In contrast to PCR analytical methods the identification can be performed without any prior knowledge and leads directly to an identification on the level of the microbe species or subspecies. No other identification method is as fast and reliable.

The invention is based, in particular, on the destruction of the different types of blood corpuscles quickly and completely in such a way that the microbes are obtained in a very pure form and endogenous blood proteins from the blood particles do not interfere with the identification. The structure of the microbes' cells is not destroyed in this process, in contrast to the blood particles. The delicate cell membrane of the blood particles includes predominantly of phospholipids, which form a membrane by non-covalent bonds. The effect of the tensides, particularly of SDS, on proteins and lipids is based particularly on breaking all non-covalent bonds and thus destroying the quaternary and tertiary structure of the cell membrane and cell structure molecules. The cell membranes and all internal cell structures thus dissolve completely, the tensides acting as solubilizers. The phospholipids of the cell membranes are themselves amphiphilic, i.e., have tenside characteristics, and can be nano-colloidally dissolved by other tensides by forming micelles. The internal structures of the blood particles, including the membrane of the cell nucleus and the chromosomes of the leukocytes, are also destroyed by SDS and widely dissolved. All these dissolved components are removed with the supernatant after the centrifugation or by micro-filtration.

The cell walls of bacteria, on the other hand, are very stable; they include mainly covalently cross-linked and thus polymerized mureins (peptidoglycans). For gram-positive bacteria there is an additional cross-linking with teichoic acids, which are also polymerized. These covalently bound meshes withstand the dissolving effect of the tensides at least for the short time of several minutes. For the subsequent mass spectrometric identification it is irrelevant whether the microbes die or not in this method, as long as the proteins in the inside are not released or changed in their primary structure. For many microbes, however, this short-term method still leaves sufficient microbes alive and able to reproduce for a further cultivation.

The method is surprisingly simple. The identification of the isolated microbes thus obtained follows conventional methods, which, however, normally are based on an isolation of one type of microbe by growing a separated colony on a cultivation medium The isolation here exists automatically because, for acute infections, only one or at most two species of microbe are found as pathogens. This means that separating these microbes from infected blood provides quantities of microbes which represent sufficiently pure microbe cultures (isolates). Even when two species of microbe are present the method still works satisfactorily.

To simplify the method of identification of microbes in blood, analysis kits with ready-to-use mixtures of tensides and defoamers may be produced and made commercially available. The mixtures may contain additionally anticoagulants and nucleases; sterile portions of these mixtures may be contained in ready-to-use evacuated centrifugation cups, easily to be filled with blood samples. The analysis kit may further comprise purified solutions for protein extraction from deposited microbes, and matrix solutions for the sample preparation on mass spectrometric sample support plates. Even one-way mass spectrometric sample support plates may be comprised in this analysis kit.

If the method of separating and isolating microbes is carried out with more centrifuge tubes than are necessary for the identification, with a dozen centrifuge tubes, for example, some of the isolated microbe deposits can also be used for further diagnostic purposes—to determine the resistance of the microbes, for example, using the conventional functional methods of trial cultivation in the presence of antibiotics.

The method of separating microbe accumulations from endogenous cells can not only be applied to blood, but also to abscesses or other foci of inflammation, since they also contain endogenous cells. One example of this is a suppurative focus, i.e., an accumulation of some living, some partially digested microbes in a mixture with certain types of leukocytes which fight them. In this case, also, the endogenous cells can be dissolved by tenside solutions. A further example is inflamed nasal mucus, which is obtained as a swab of the nasal mucosa and where the identification of the microbes is of very great interest. These types of sample can also be obtained from other mucous membranes.

In the method described above the mass spectra of the microbes were acquired in mass spectrometers with ionization by matrix-assisted laser desorption (MALDI). This is the usual way, but not necessarily the only one. The solutions of soluble proteins from microbes can also be ionized by electrospraying, for example. This type of ionization generates strong superimpositions of multiply charged ions in the mass range of about 600 to 1,600 daltons, which necessarily requires a mass spectrometer with high resolution. Time-of-flight mass spectrometers with orthogonal injection of the ions (OTOF-MS) can be used as the mass spectrometer, as can ion cyclotron resonance mass spectrometers (ICR-MS) or other high-resolution mass spectrometers.

The different charge levels of the ions formed by electrospray ionization can be combined mathematically in order to obtain a microbe spectrum. It is also possible to conduct a physical charge reduction, however. This involves bringing together positively charged protein ions and suitable negatively charged ions in an ion reactor located between electrospray ion source and analyzer, resulting in a deprotonation of the protein ions. These are introduced into the mass spectrometer, which must be able to cope with a large range of masses, however.

Further methods of ionization are also known and can be used here. An advantageous method is atmospheric pressure chemical ionization (APCI), for example. The molecules are introduced to the chemical ionization by atomizing a liquid and vaporizing the droplets, or by weak, non-ionizing laser desorption ("laser ablation"). The chemical ionization supplies practically only singly charged ions and is thus very favorable, but also requires a mass spectrometer with sufficiently large mass range.

By knowledge of the invention, the methods described here can be modified by those skilled in the art in a wide variety of ways. Some of these modifications have already been described above; there are also additional methods which can generate the desired informative mass spectra of the microbes for their identification on the fundamental basis of direct separation of the microbes from blood, abscesses or other inflamed tissue.

Although the present invention has been illustrated and described with respect to several preferred embodiments thereof, various changes, omissions and additions to the form and detail thereof, may be made therein, without departing from the spirit and scope of the invention.

What is claimed is:

1. A method for the mass spectrometric identification of microbes comprising bacteria and yeast in blood in which the microbes are deposited by centrifuging or by filtration, after which a mass spectrum is acquired from the microbes and said microbes are identified by the mass spectrum, characterized by dissolving the blood particles of a blood sample from a blood culture by adding a tenside prior to the deposition of the microbes.

2. A method for the mass spectrometric identification of microbes comprising bacteria and yeast in blood in which the microbes are deposited by sedimentation or by micro-filtration, after which a mass spectrum is acquired from the microbes and said microbes are identified by the mass spectrum, characterized by dissolving the blood particles of a blood sample from a blood culture by adding a tenside prior to deposition of the microbes.

3. A method for the mass spectrometric identification of microbes comprising bacteria and yeast in blood in which the microbes are pelleted by centrifuging or by filtration, after which a mass spectrum is acquired from the microbes and said microbes are identified by the mass spectrum, characterized by dissolving the blood particles of a blood sample from a blood culture by adding a tenside prior to pelleting of the microbes.

4. The method of claim 1, wherein sufficient numbers of microbes in the blood are produced by cultivation.

5. The method of claim 1, wherein the microbes deposited by centrifugation are washed and again centrifuged.

6. The method of claim 1, wherein the tenside is added as a solution.

7. The method of claim 1, wherein an anticoagulant is added to the blood sample.

8. The method of claim 1, wherein one or more nucleases are added to the blood sample.

9. The method of claim 1, wherein the blood for the blood sample is diluted with distilled water by a dilution factor between about 1:2 and 1:10.

10. The method of claim 1, wherein the blood sample is centrifuged and the supernatant is removed before the tenside solution is added.

11. The method of claim 1, wherein the deposited microbes are disintegrated by sonication or mechanical treatment.

12. The method of claim 1, wherein the deposited microbes are disintegrated by solution containing formic acid or trifluoroethanoic acid and acetonitrile.

13. The method of claim 1, wherein the preparation of measurement samples comprises transferring some of the microbes of the deposit onto a mass spectrometric sample support where a solution with a matrix substance for matrix assisted laser desorption/ionization is added.

14. The method of claim 5, wherein sodium dodecyl sulfate (SDS) is used as the tenside.

15. The method of claim 6, wherein the tenside solution contains a defoamer.

16. The method of claim 5, wherein the solution is about a 5 to 20% aqueous sodium dodecyl sulfate (SDS) solution.

17. The method of claim 9, wherein the blood for the blood sample is diluted with distilled water by a dilution factor of about 1:5.

18. The method of claim 12, wherein the preparation of measurement samples on a mass spectrometric sample support plate is performed using a matrix substance for matrix assisted laser desorption/ionization in whose crystals the soluble proteins of the disintegrated microbes are embedded.

19. The method of claim 18, wherein the mass spectrometric measurement is performed in a time-of-flight mass spectrometer with ionization by matrix assisted laser desorption (MALDI).

* * * * *